United States Patent [19]
Shikinami et al.

[11] Patent Number: 5,298,602
[45] Date of Patent: Mar. 29, 1994

[54] POLYMERIC PIEZOELECTRIC MATERIAL

[75] Inventors: Yasuo Shikinami; Kunihiro Hata, both of Osaka, Japan

[73] Assignee: Takiron Company, Ltd., Osaka, Japan

[21] Appl. No.: 10,165

[22] Filed: Jan. 28, 1993

[30] Foreign Application Priority Data

Nov. 6, 1992 [JP] Japan .................................. 4-322519
Nov. 6, 1992 [JP] Japan .................................. 4-322520

[51] Int. Cl.$^5$ .................. C08G 63/06; A61F 2/28; H04R 17/00
[52] U.S. Cl. .................. 528/361; 29/25.35; 29/594; 29/595; 252/62.9; 623/16
[58] Field of Search ............. 29/25.35, 594, 595; 252/62.9; 528/361

[56] References Cited

U.S. PATENT DOCUMENTS

| | | | |
|---|---|---|---|
| 4,322,877 | 4/1982 | Taylor | 29/25.35 |
| 4,578,384 | 3/1986 | Hollinger | 424/22 |
| 4,798,206 | 1/1989 | Maddison et al. | 128/419 |
| 4,921,928 | 5/1990 | Tanino et al. | 528/361 |
| 4,959,439 | 9/1990 | Tanino et al. | 528/361 |
| 5,131,276 | 7/1992 | Kibblewhite | 29/595 |

FOREIGN PATENT DOCUMENTS 0349656 12/1988 European Pat. Off.
2729223 1/1979 Fed. Rep. of Germany.

OTHER PUBLICATIONS

Reports on Progress in Polymer Physicas in Japan, vol. XXXIV (1991), pp. 269-272, E. Fukada, "Piezoelectric Properties of Poly-L-Lactic acid".

Proc. 7th Int. Symp. Electrets (Ed. by R. Gerhard-Multhaupt, IEEE, New York, N.Y) (1991) pp. 695-705, E. Fukada, "Bioelectret and biopiezoelectricity".

Ferroelectrics, vol. 1, 1983, London, GB, J. J. Ficat et al., "Osteogenesis Induced by Bimorph Polyvinylidene Fluoride Films".

*Primary Examiner*—John Kight, III
*Assistant Examiner*—Shelley A. Dodson
*Attorney, Agent, or Firm*—Sughrue, Mion, Zinn, Macpeak & Seas

[57] ABSTRACT

A polymeric piezoelectric material including a polylactic acid molded article having been uniaxially drawn to an extent causing no fibrillation. The piezoelectric material exhibits piezoelectric properties equal to or higher than those of electret type or polypeptide type piezoelectric materials while having high enough mechanical strength to be processed into various articles ranging from films to profiles depending on the end use.

19 Claims, 7 Drawing Sheets

POLYMERIC PIEZOELECTRIC MATERIAL

FIELD OF THE INVENTION

This invention relates to a polymeric piezoelectric material which is expected to be applied to various fields, such as implant devices for the acceleration of ossification, ultrasonic transducers for medical use, sound transducers, measuring instruments, ultrasonic wave applied measuring instruments, piezoelectric oscillators, mechanical filters, piezoelectric transformers, and the like. More particularly, it relates to a polymeric piezoelectric material comprising a polylactic acid molded article having been uniaxially drawn to an extent causing no fibrillation.

BACKGROUND OF THE INVENTION

Known piezoelectric polymers include a polypeptide type, such as poly($\gamma$-benzyl L-glutamate); an electret type, such as polyvinyl chloride; and a ferroelectric substance type, such as polyvinylidene fluoride, a vinylidene fluoridetrifluoroethylene copolymer, and a vinylidene cyanide-vinyl acetate copolymer. The most typical among them is a film of polyvinylidene fluoride, which has already been put to practical use in ultrasonic transducers (see JP-A-55-151896 and JP-A-56-112200 (the term "JP-A" as used herein means an "unexamined published Japanese patent application")).

Polyvinylidene fluoride, a vinylidene fluoridetrifluoroethylene copolymer, and a vinylidene cyanide-vinyl acetate copolymer, which are synthetic polar piezoelectric polymers of the ferroelectric substance type, are oriented by drawing and the application of an electrical field. The mechanism of retention is spontaneous polarization or freeze-polarization, and the orientation state is uniaxial polar orientation. A drawing treatment and a polarizing treatment are required before these materials exhibit piezoelectric properties. In particular, polyvinylidene fluoride has the highest piezoelectric properties. However, it has a dielectric constant of 13, which is relatively high as compared with other polymeric materials, so that the piezo g-constant (open circuit voltage per unit stress) obtained by dividing a piezo d-constant by a dielectric constant is not so great. Therefore, it has somewhat poor sound-to-electricity transformation efficiency, although it has satisfactory electricity-to-sound transformation efficiency.

Films of electret type polymers, such as polyvinyl chloride, are endowed with piezoelectric properties by orientation of the polar groups by polarizing treatment. Piezoelectricity of these materials is not as high as the polymers of the ferroelectric substance type.

To the contrary, artificial oriented films of naturally-occurring polymer-related substances, such as poly($\gamma$-benzyl L-glutamate) which are of the polypeptide type, DNA, and polyhydroxybutyrate, have their orientation controlled by dynamic drawing. The mechanism of retention is a crystal structure, and the state of orientation is uniaxial orientation with no polarity. These films exhibit piezoelectric properties without being subjected to polarizing treatment in such a manner that polarization takes place in the z direction upon application of shear in the xy directions. However, since they have a molecular structure in which a main chain helix is surrounded by a long side chain, their piezoelectric properties are of the relaxation type and are not so strong. Further, since the mechanical strength of these materials themselves is insufficient, it is difficult to obtain rigid piezoelectric materials of irregular shape.

With respect to the artificial oriented film of polyhydroxybutyrate, there is a research report that piezoelectricity of the film wound around a fractured part of a bone is advantageous of for acceleration of the initial ossification (Shigeru Harada, et al., *The 12th Research Meeting on Bone and Electrical Stimulation*, No. 8 (1985)). However, the fact that the film has small piezoelectric constants $d'_{14}$ of about 1.3 (pC/N) and $e'_{14}$ of 3.5 to 4.0 (mC/m$^2$) at room temperature and 10 Hz leaves doubt as to whether the piezoelectricity of the film makes a true contribution to the ossification in the initial stage. Even if it does, it seems that a remarkable effect on the acceleration of ossification would hardly be produced. Further, the artificial oriented film of polyhydroxybutyrate so slowly degrades in a living body that it remains unabsorbed for a long time even after a fracture completely heals. Besides, the safety of polyhydroxybutyrate in a living body has not yet been confirmed.

SUMMARY OF THE INVENTION

An object of the present invention is to provide a polymeric piezoelectric material which requires no polarizing treatment for exhibition of piezoelectric properties, which has a lower dielectric constant than that of polyvinylidene fluoride, etc., which has piezoelectric properties equal to or higher than those of piezoelectric materials of the electret type or polypeptide type, and which has high mechanical strength and can be processed into various articles ranging from films to profiles depending on the end use.

Another object of the present invention is to provide a film of a polymeric piezoelectric material which produces a remarkable effect on the acceleration of ossification and which is rapidly absorbed into a living body after the healing of a fracture of a bone and is therefore very safe.

A further object of the present invention is to provide a polymeric piezoelectric material which can be applied to various instruments as ultrasonic transducers, ultrasonic probes, etc.

As a result of extensive investigations, the inventors have found that the above objects of the present invention are accomplished by a polymeric piezoelectric material comprising a polylactic acid molded article having been uniaxially drawn to an extent causing no fibrillation.

Other objects, characteristics, and advantages of the present invention will be apparent from the detailed description hereinafter given.

DETAILED DESCRIPTION OF THE INVENTION

Polylactic acid which can be used in the present invention is a biodegradable and bioabsorbable high polymer obtained by synthesizing a lactide, a cyclic dimer of lactic acid, from optically active L- or D-lactic acid by a known process (see U.S. Pat. No. 2,668,182 to C. E. Love) and conducting ring-opening polymerization of the lactide. The polylactic acid may be either a homopolymer of L- or D-lactic acid or a block copolymer of L-lactic acid and D-lactic acid. Since the piezoelectric properties of the latter polymer are reduced depending on the L-form to D-form ratio, the former polymer is more advantageous unless either one of the L- and D-forms overwhelms the other in ratio.

The molecular weight of the polylactic acid is not particularly limited as long as it allows melt molding and drawing. A reduction in molecular weight on melt molding or desired strength of a polymeric piezoelectric material for practical use being taken into consideration, it is preferable to use polylactic acid having a viscosity-average molecular weight of at least about 50,000, and preferably about 100,000 or more. While polylactic acid of high molecular weight is suitable for obtaining high strength materials, polylactic acid having too high of a molecular weight requires a high temperature and a high pressure for melt molding, which leads to a great reduction in molecular weight, resulting a failure to obtain a high strength material. Accordingly, the viscosity-average molecular weight of the polylactic acid is preferably up to about 1,000,000 and more preferably up to about 500,000.

The polymeric piezoelectric material of the present invention can be obtained by a process comprising melt-molding the above-mentioned polylactic acid into a rod, a plate, etc. by, for example, extrusion or press molding, followed by uniaxially drawing to an extent causing no fibrillation, or a process comprising casting a solution of the polylactic acid in an organic solvent on a carrier, evaporating the solvent to obtain a cast film, and uniaxially drawing the film to an extent causing no fibrillation.

The conditions for melt molding are selected appropriately depending on the molecular weight (or melting point) of the polylactic acid, the method of melt molding, and the like. For example, extrusion is desirably carried out by using an ordinary extruder under the following temperature and pressure conditions.

The extrusion temperature is set between the melting point of polylactic acid and about 220° C. Extrusion is difficult at temperatures below the melting point. At temperatures exceeding about 220° C., the molecular weight is considerably reduced due to heat instability of the polylactic acid, tending to result in a failure to obtain a high strength piezoelectric material. Where polylactic acid having a molecular weight of from about 100,000 to about 500,000 is used, the extrusion temperature is preferably about 200° C. or lower.

Likewise, the extrusion pressure is preferably set as low as possible within a range allowing extrusion in order to minimize a molecular weight reduction. The possible lowest pressure can be determined according to the melt viscosity (molecular weight) of the polylactic acid used. In using polylactic acid having a molecular weight of from about 100,000 to about 500,000, a suitable extrusion pressure is between about 170 and 210 kg/cm$^2$.

Film casting is preferably carried out by completely dissolving polylactic acid in an organic solvent, such as dichloromethane, at room temperature, casting the solution on a carrier, and evaporating the solvent at room temperature under normal pressure.

The thus-obtained molded article, such as a rod, a plate, or a film, shows no piezoelectric properties because the polymer molecules as such are not oriented. The molded article is then subjected to uniaxial drawing in a longitudinal direction, e.g., the extrusion direction, in a heated nitrogen stream to thereby orient the polymer molecules to impart piezoelectric properties and, at the same time, increase the mechanical strength. The uniaxial drawing can be carried out at a temperature of from about 60° to 180° C., and preferably from about 80° to 160° C. While a possible upper limit of a draw ratio is about 10, too high of a draw ratio tends to cause fibrillation only to provide a porous material which does not exhibit any piezoelectric properties due to movement among fibrils. The fibrillation is a phenomenon that a filament, a fiber, etc. is separated into fibrils (fibrils are minute fibers which constitute a fiber and have a radius of, though there are various views, about from 0.1 to 1.4 μm). Filaments, uniaxially drawn films and the like sometimes split along the drawing direction by strong tensile force or shear force since their molecules are oriented along the drawing direction, and the fibrillation occurs frequently in such a case. Accordingly, a high draw ratio tends to cause fibrillation due to the high degree of molecular orientation. If the draw ratio is too small, on the other hand, molecular orientation of the polylactic acid is insufficient, resulting in a reduced piezoelectric constant. Accordingly, a preferred draw ratio ranges from about 3 to about 6, at which no fibrillation can be achieved. The polylactic acid molded article uniaxially drawn at such a preferred draw ratio exhibits high piezoelectric properties, such as having a piezoelectric constant $-d'_{14}$ of about 8 to 13 pC/N and $-e'_{14}$ of about 10 to 20 mC/m$^2$. With piezoelectric properties, mechanical strength, and other physical properties being taken into consideration, the best draw ratio ranges from about 4 to about 5.

In the thus-uniaxially drawn polylactic acid molded article, C=O and C—H in the molecular main chains adjacent to each other by molecular orientation are linked through a hydrogen bond in the direction crossing the main chain, and a non-polar methyl group as a side chain causes little relaxation effect. As a result, the uniaxially drawn polylactic acid molded article exhibits piezoelectric properties equal to or higher than those of conventional polypeptide type or electret type piezoelectric materials as proved by the data given in Examples hereinafter described. For example, polyvinylidene fluoride of the dielectric substance type whose piezoelectric constant is the highest of organic polymers has a $d_{31}$ of 24 (pC/N) and a $d_{33}$ of $-36$ (pC/N), giving a g constant ($d/\epsilon$, indicative of open voltage per unit stress) $g_{31}$ of 0.21 and $g_{33}$ of $-3.1$, whereas the above-mentioned polylactic acid, having a dielectric constant $\epsilon$ of 3.5, gives $d'_{14}/\epsilon = 2.3$ to 3.7, affording higher voltage sensitivity than polyvinylidene fluoride.

Figure 1:
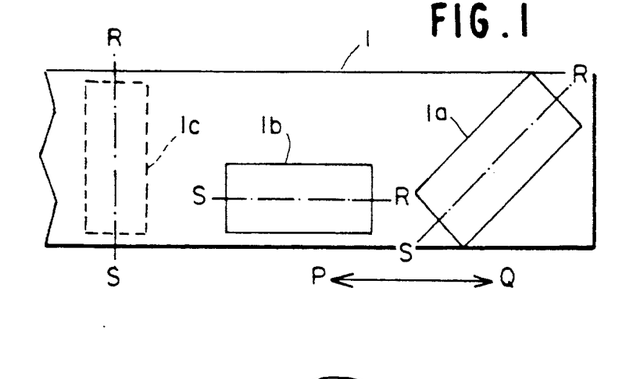
FIG. 1 illustrates a cutting mode of a film of the polymeric piezoelectric material according to the present invention.

The uniaxially drawn polylactic acid molded article is cut and processed while giving consideration to its drawing direction to provide a polymeric piezoelectric material of any shape and size according to the end use. In the case of a cast film, for example, as shown in FIG. 1 drawn film 1 may be cut diagonally or parallel to the drawing direction (hereinafter referred to as the PQ direction) to obtain piezoelectric film 1a or 1b which can be applied to a fracture of a bone for ossification acceleration. The axial direction connecting both ends of film 1a or 1b (hereinafter referred to as the RS direction) and the PQ direction do not make right angles. The above-mentioned cutting mode with the directions RS and PQ making no right angles is based on the following reason.

The piezoelectricity effect of the polylactic acid uniaxially drawn film is of the same kind as the shear piezoelectricity effect inherent in the crystals and oriented molecules of a uniaxially oriented optically active polymer, which is piezoelectricity of the relaxation type developed on crystal boundaries. Therefore, when an outer force is applied to both ends of the film to cause deformation, charges are generated on the crystal surface in proportion to the outer force to generate a voltage. Conversely, when a voltage is applied to the crystal, the crystal undergoes deformation in proportion to the applied voltage. In a uniaxially oriented crystal system, the shear deformation efficiency becomes highest where the crystal is uniaxially oriented at a geometric angle of 45° with the RS direction. Shear deformation cannot take place theoretically when an outer force is uniformly applied to both ends of a film in which the RS direction is the same as the PQ direction. However, it seems that slight shear deformation takes place among crystals partly because of local morphological unevenness in terms of, e.g., a crystalline phase to amorphous phase ratio of the polymer and partly because of impracticability of applying a uniform outer force to both ends of a film in parallel to the crystal phase. Where the RS direction and the PQ direction make an angle of 90° in a film, even if an outer force is uniformly applied to both ends of the film, it only follows that the distance among crystals changes without any positional shear, theoretically causing no shear deformation. This is the case where a shear piezoelectricity effect is the least expected. As long as the RS and PQ directions form an angle of 0° or more and less than 90°, the shear piezoelectricity effect becomes greater at an angle causing a greater shear effect. Accordingly, it is film 1a cut out in such a manner that the RS direction and the PQ direction form an acute angle, particularly about 45°, that exhibits the most pronounced piezoelectricity effect. Next to this film is film 1b cut out in such a manner that the RS direction and the PQ direction are parallel to each other (forming an angle of 0°). Film 1c indicated by the dotted line in FIG. 1 which is cut out in such a manner that the RS and PQ directions make a right angle (90°) ought to develop no substantial piezoelectricity effect.

For use as a piezoelectric film for ossification acceleration, films having a rectangular shape, such as films 1a and 1b shown in FIG. 1, are applied to a fractured bone with their ends in the longitudinal direction being fixed as hereinafter described. Accordingly, it is highly desirable for these rectangular films that the PQ direction and the RS direction form any angle except 90°. Films having an oval or ellipsoidal shape are also applied to a fractured bone with their ends in the longitudinal direction being fixed and is also highly desirable for these oval or ellipsoidal films that the PQ direction and the RS direction form any angle except 90°. On the other hand, in using a film having a square shape, either one of the two pairs of facing sides thereof are fixed. In this case, the PQ direction and the axis connecting the facing sides should desirably form any angle except 90°. Similarly, in the cases of films having a regular polygonal shape, such as a regular hexagonal shape or a regular octagonal shape, the PQ direction and an axis connecting any one of the pairs of facing sides should form any angle except 90°.

When piezoelectric film 1a or 1b is applied to a fractured bone for ossification acceleration, it is desired that the film should have a thickness ranging from about 50 to 500 μm, and preferably from about 100 to 300 μm. If the film thickness is less than about 50 μm, the film will degrade before the healing of a fracture which usually takes about 8 to 12 weeks to heal. If the film thickness exceeds about 500 μm, the excessive rigidity makes it difficult to apply the film in conformity to the shape of the bone, and the fixed film hardly undergoes deformation with a small outer force.

The rod-shaped or plate-shaped polylactic acid uniaxially drawn articles of the present invention may be cut out at a certain angle against the drawing direction and processed to have a desired size, shape, and thickness. The thus-cut articles are useful as piezoelectric elements, such as an ultrasonic transducer, an ultrasonic probe, etc., for ultrasonic diagnostic devices, ultrasonic flaw detectors, etc.

For use as the above-described piezoelectric elements, e.g., an ultrasonic transducer or an ultrasonic probe, it is desired that a large piezoelectricity effect should be developed by deformation or oscillation in the thickness direction of the element. To this effect, it is preferable that the thickness direction and the drawing direction of the element should form an angle other than 90° so that the deformation in the thickness direction may bring about great shear deformation of the oriented molecules of polylactic acid. As is understood from the above explanation of the cutting mode of a uniaxially drawn film, the greatest piezoelectricity effect can be obtained when the direction of deformation and the drawing direction form an angle of about 45°. However, in the case of the uniaxially drawn film, the thickness direction and the drawing direction form right angles irrespective of the cutting direction. Such a film shows a great piezoelectricity effect on application of deformation parallel to the film surface but has a small piezoelectricity effect when deformed in the thickness direction.

In contrast, in the case of rod-shaped or plate-shaped molded articles, it is possible to cut an element out of the molded article in such a manner that the thickness direction may form an angle other than 90° with the drawing direction to thereby obtain an element capable of showing a great piezoelectricity effect upon deformation in the thickness direction. That is, when the resulting element undergoes deformation in its thickness direction, charges are generated in the direction perpendicular to the direction of deformation due to the great shear deformation of the oriented molecules to thereby generate a voltage. Conversely, application of voltage results in deformation in the thickness direction. Such a piezoelectricity effect can be utilized in the above-mentioned uses.

In addition, the rod-shaped or plate-shaped drawn articles cut to an appropriate length are also useful as intramedullary nails or plates having an ossification accelerating effect for osteosynthesis.

The present invention will now be illustrated in greater detail with reference to Examples, but it should be understood that the present invention is not construed as being limited thereto. Unless otherwise indicated, all parts, percents, ratios and the like are by weight.

EXAMPLE 1

25 g of poly-L-lactic acid having a viscosity-average molecular weight of 330,000 (in chloroform at 25° C.) was completely dissolved in 1000 ml of dichloromethane by stirring with a magnetic stirrer at room temperature for 6 hours. The solution was cast on a carrier, and the solvent was evaporated at room temperature under normal pressure to obtain a film of poly-L-lactic acid.

The film was cut to a width of 3 to 4 cm and allowed to stand in a thermostat set at 108° C. in a nitrogen atmosphere for 2 minutes. The film was then drawn at a draw ratio of 4, followed by annealing for 2 minutes to obtain a 180 μm thick drawn film.

The drawn film was diagonally cut into a rectangle in such a manner that the RS direction and the PQ direction formed an angle of 45° as shown in FIG. 1 to obtain film 1a for ossification acceleration having a length of 1.64 cm and a width of 1 cm.

The complex piezoelectric constants $d_{14}$ ($d'_{14} - id''_{14}$) and $e_{14}$ ($e'_{14} - ie''_{14}$), the complex dielectric constant $\epsilon$ ($\epsilon' - i\epsilon''$), and the complex elastic constant c ($c' + ic''$) of the film were measured at a frequency of 9.76 Hz by means of a piezoelectricity meter ("Rheolographsolid S-1" manufactured by Toyo Seiki Seisakusho). The results obtained are shown in FIGS. 2 to 5, respectively.

Figure 2:
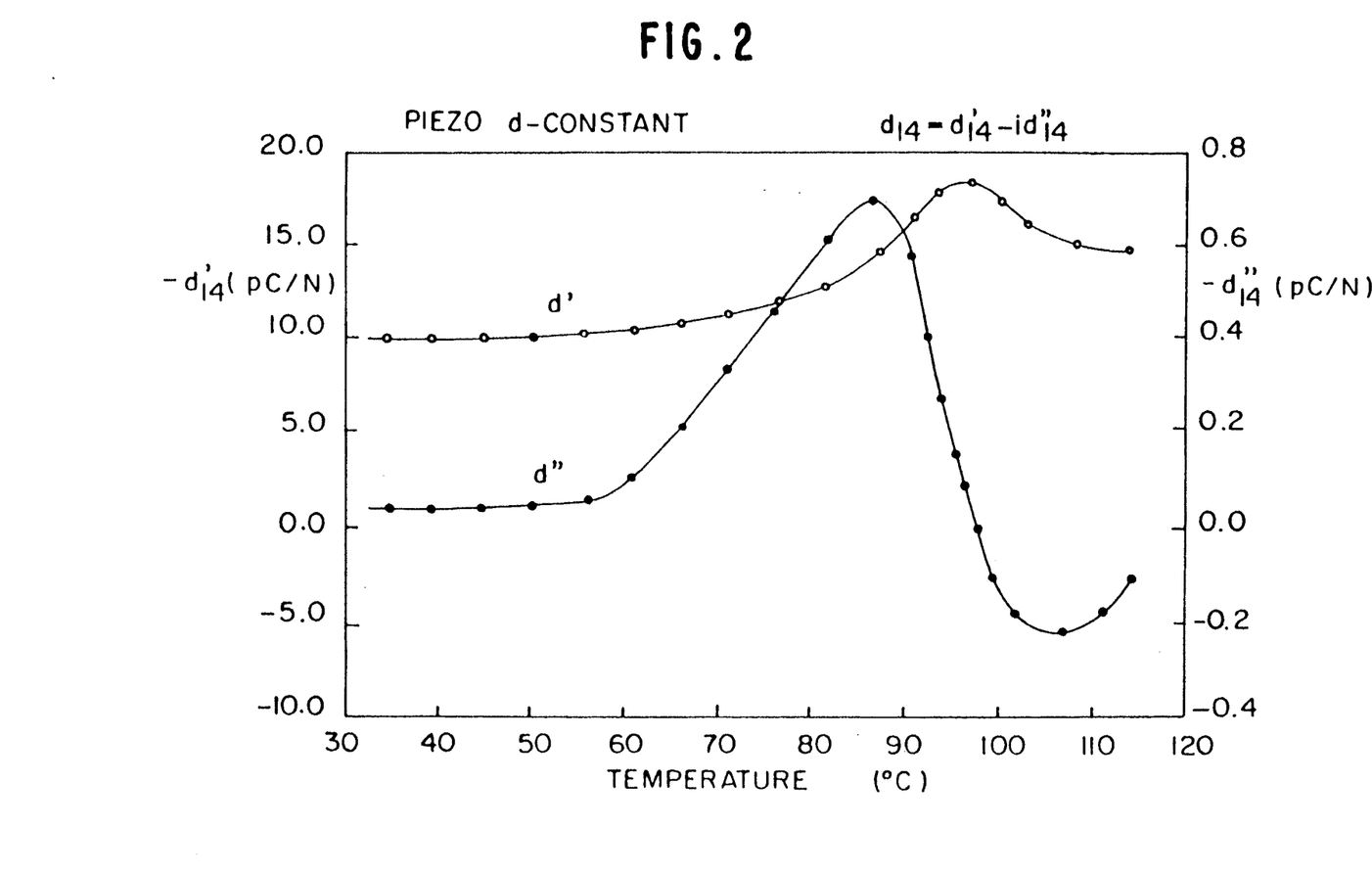
FIG. 2 is a plot of piezo d-constant vs. temperature of a film of the polymeric piezoelectric material according to the present invention.
Figure 3:
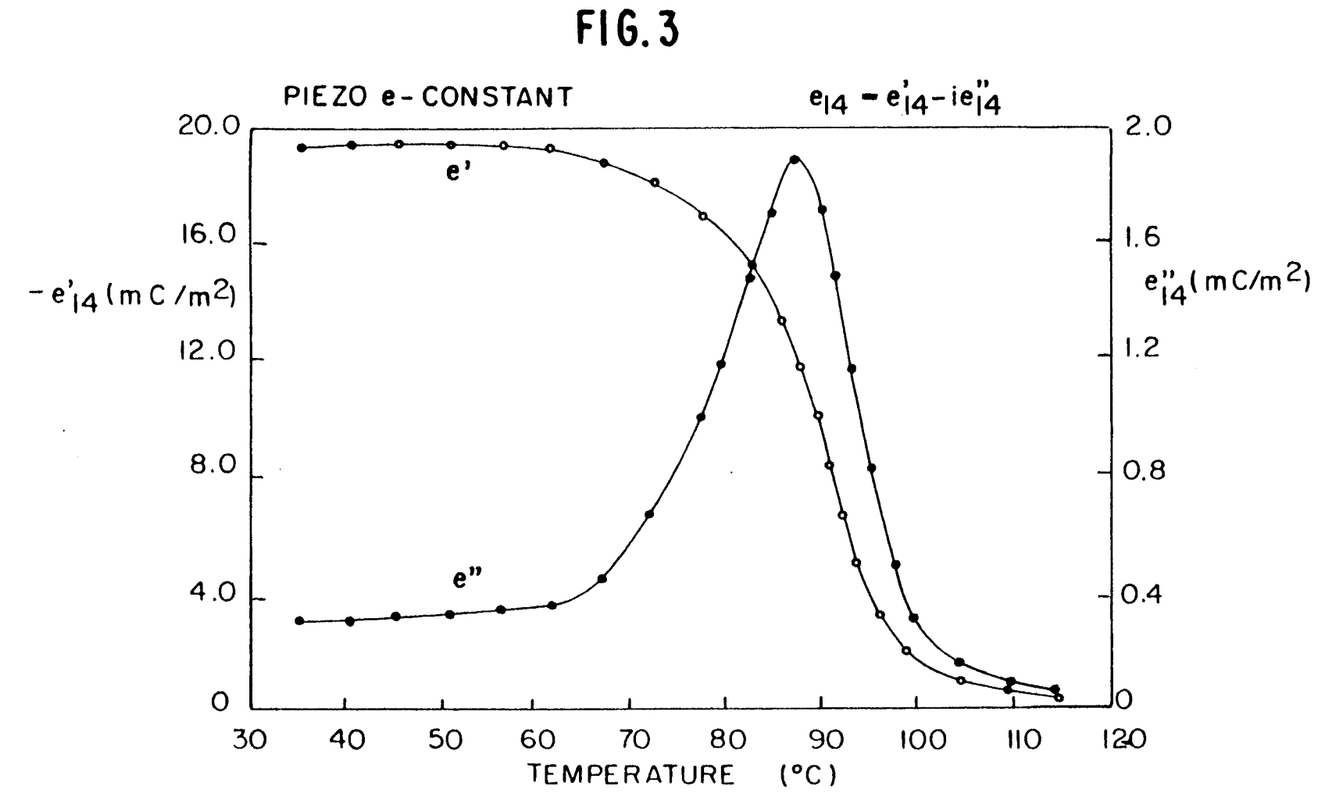
FIG. 3 is a plot of piezo e-constant vs. temperature of a film of the polymeric piezoelectric material according to the present invention.

FIGS. 2 and 3 show the piezo d-constant and piezo e-constant, respectively, plotted against temperature. FIG. 2 reveals that the piezoelectricity of stress constant ($-d'_{14}$) ranges from about $10 \times 10^{-12}$ to $20 \times 10^{-12}$ C/N in a temperature range of from 30° to 115° C. In a temperature range of from about 85° to about 90° C, $-d'_{14}$ increases, and $-d''_{14}$ reaches its peak. These results are assigned to the dynamic relaxation due to initiation of the microbrownian movement of the molecular chain. FIG. 3 reveals that the piezoelectricity of strain constant ($-e'_{14}$) is from about $19 \times 10^{-3}$ to $20 \times 10^{-3}$ C/m$^2$ at around room temperature, and $-e''_{14}$ reaches its peak at around 85° to 90° C. similarly to $-d''_{14}$.

Figure 4:
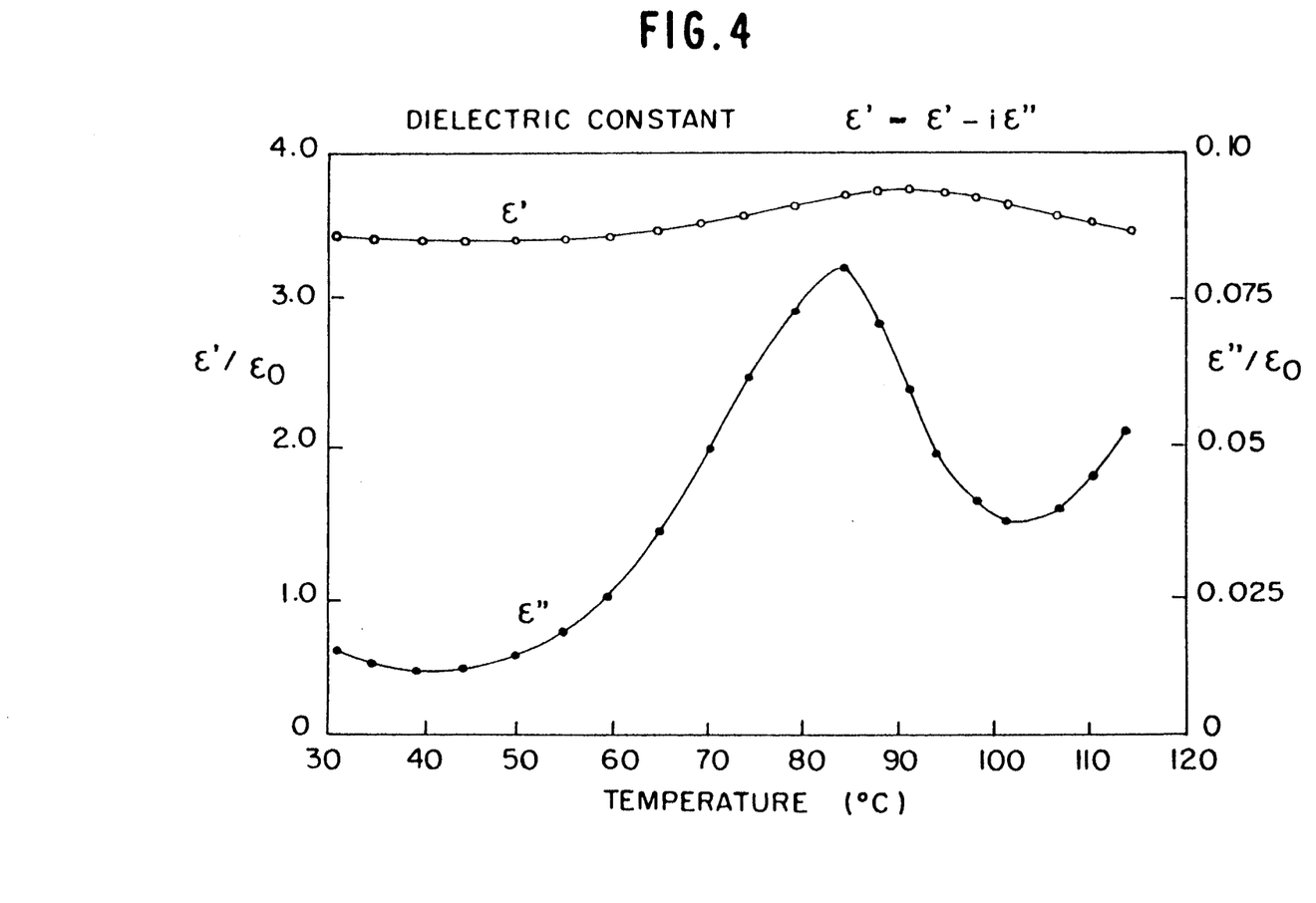
FIG. 4 is a plot of dielectric constant vs. temperature of a film of the polymeric piezoelectric material according to the present invention.

FIG. 4 shows a plot of dielectric constant vs. temperature. The dielectric constant $\epsilon'$ is about 3.5, and the dielectric loss $\epsilon''$ shows its peak at around 85° C.

Figure 5:
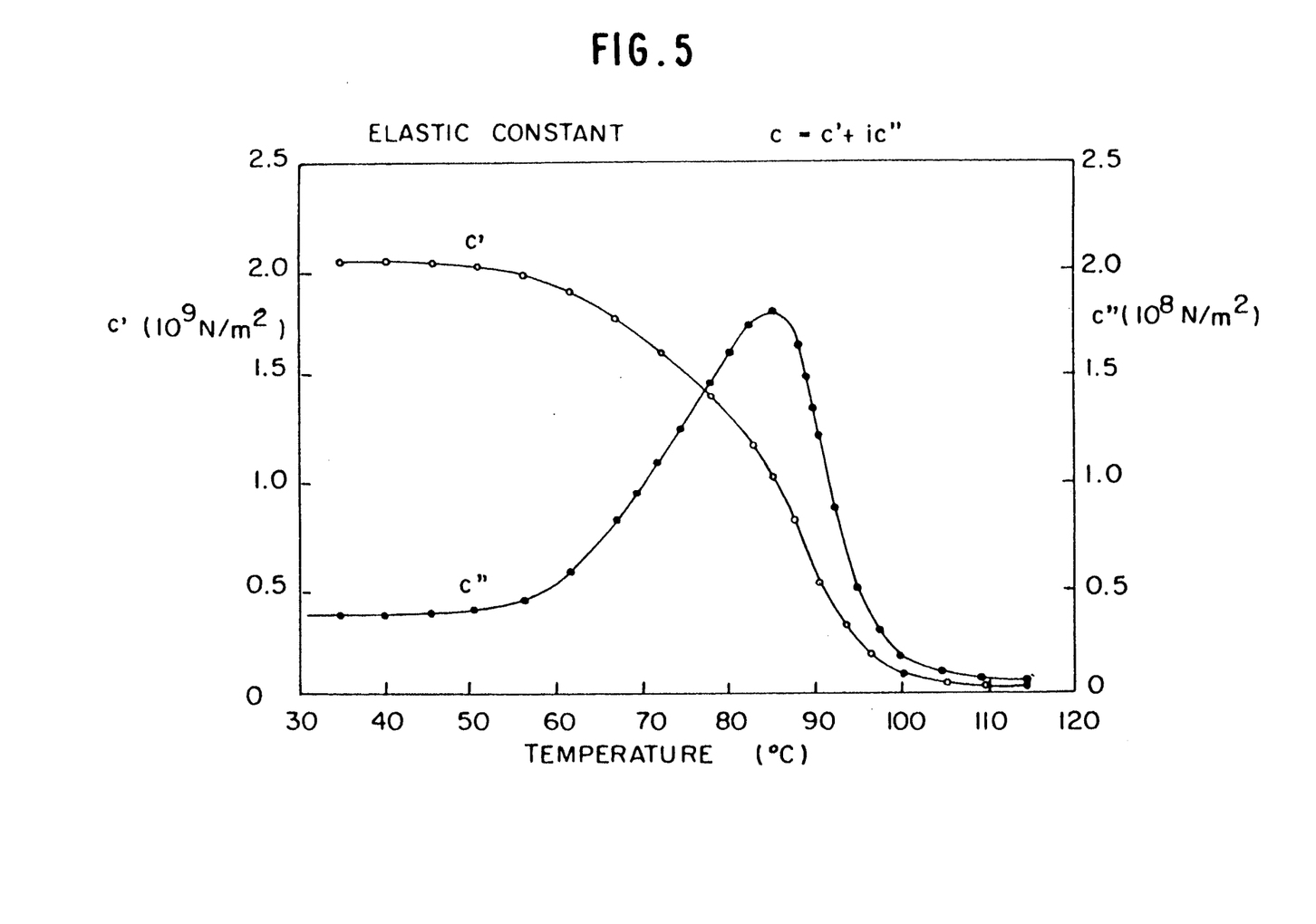
FIG. 5 is a plot of elastic constant vs. temperature of a film of the polymeric piezoelectric material according to the present invention.

FIG. 5 shows a plot of elastic constant vs. temperature. The elastic constant $c'$ at around room temperature is about $2 \times 10^9$ N/m$^2$, and $c''$ reaches its peak due to the dynamic relaxation at around 85° C. similarly to the piezoelectricity constants and dielectric constant.

The piezoelectric properties, dielectric properties, and dynamic viscoelasticity shown in FIGS. 2 through 5 are each closely related to the molecular movement of the polymer and can be treated as a relaxation phenomenon. The peaks of $d''$, $e''$, $\epsilon''$, and $c''$ in the temperature range between 85° and 90° C. are all attributed to the dynamic relaxation due to the microbrownian movement of the polylactic acid molecular chain. That is, the same phenomenon has been determined through various approaches.

Figure 6:
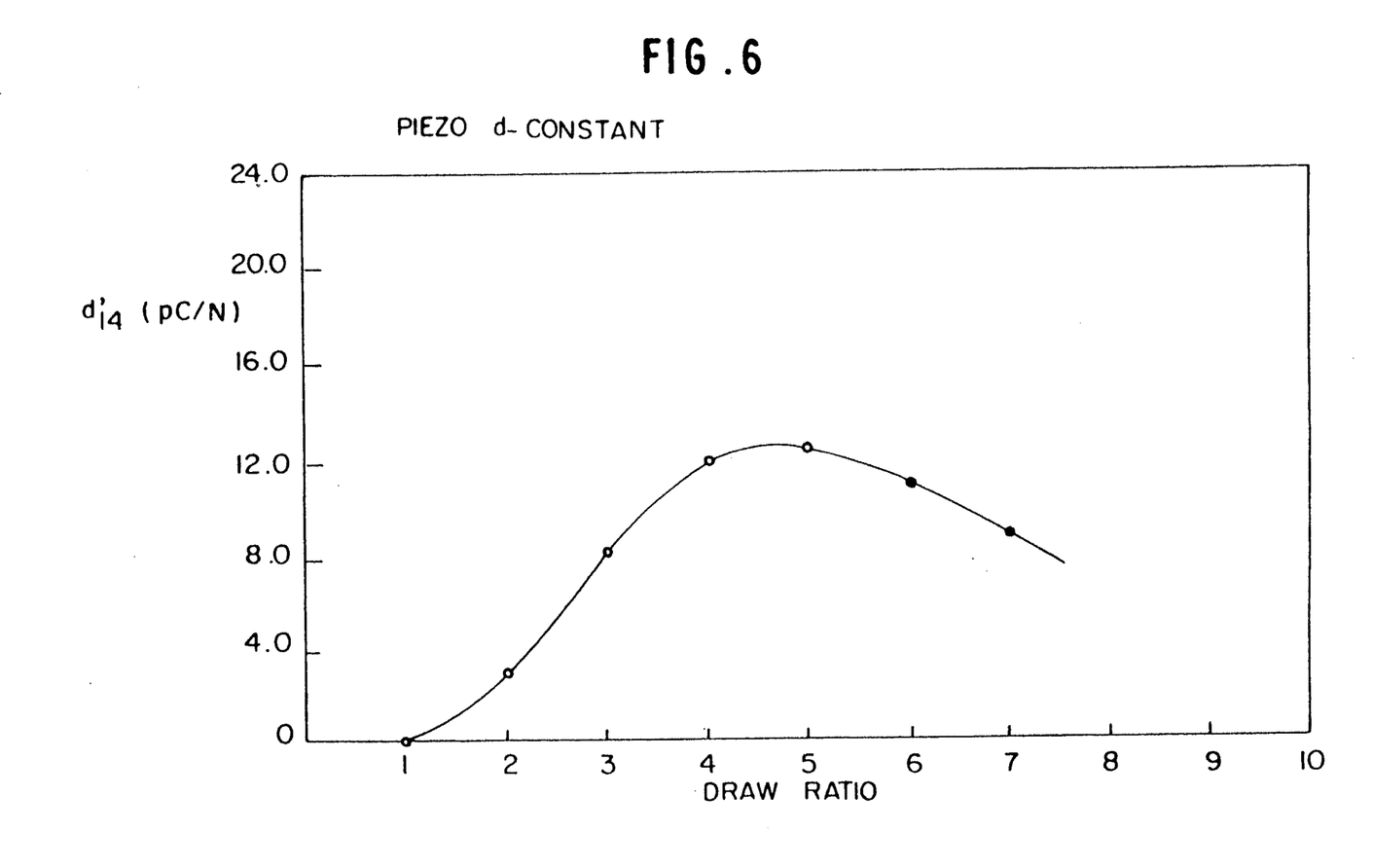
FIG. 6 is a plot of piezo d-constant vs. draw ratio of a film of the polymeric piezoelectric material according to the present invention.
Figure 7:
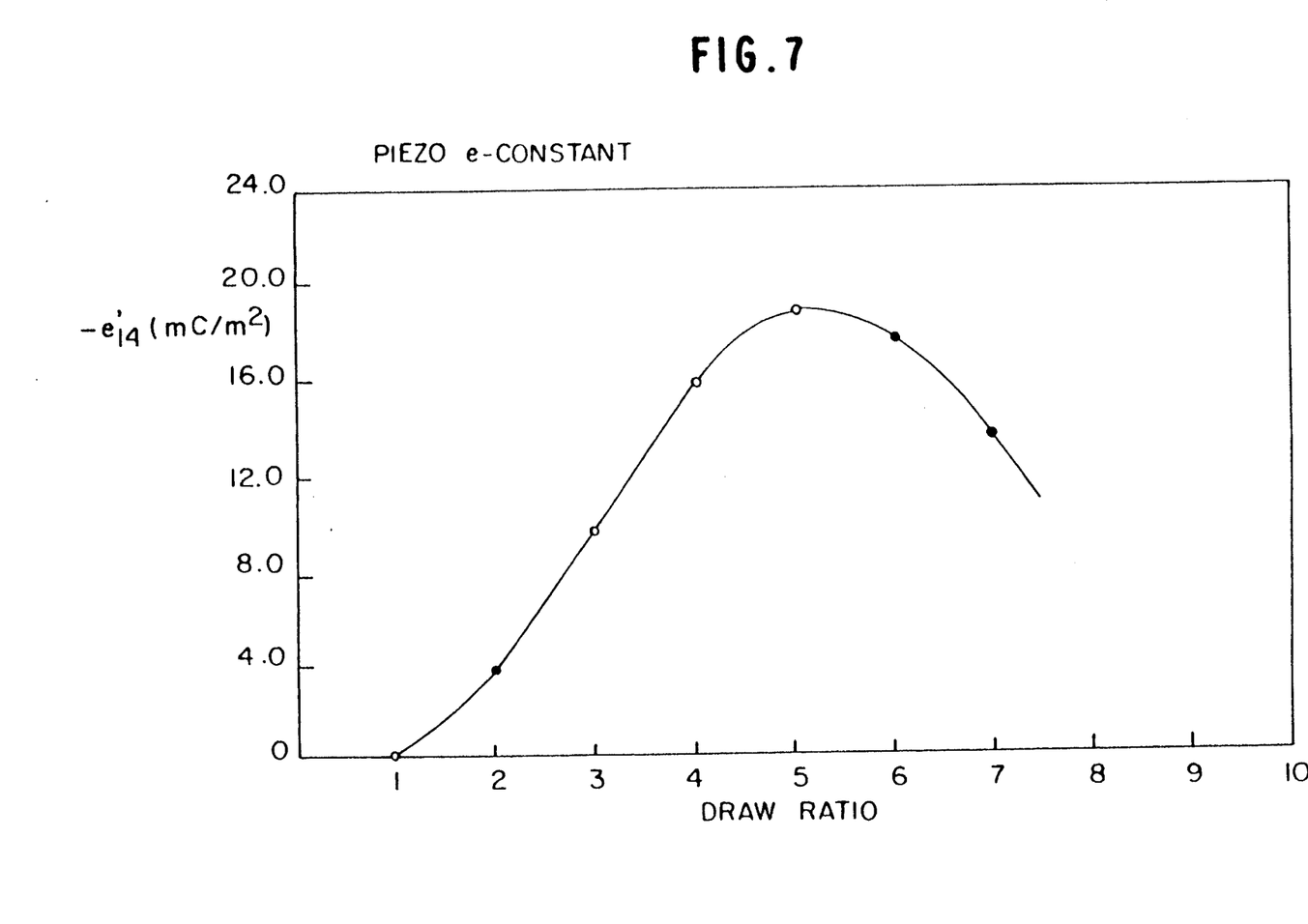
FIG. 7 is a plot of piezo e-constant vs. draw ratio of a film of the polymeric piezoelectric material according to the present invention.

A d-constant vs. draw ratio plot and an e-constant vs. draw ratio plot are shown in FIGS. 6 and 7, respectively. All these results are for a film cut out at an angle of 45° with the drawing direction. It is seen that the d-constant and the e-constant reach their respective peaks at a draw ratio of from 4 to 5 and at a draw ratio of from 4 to 6, respectively. These peak values are about 10 times and about 5 times, respectively, those of a drawn film of polyhydroxybutyrate.

EXAMPLE 2

A 1.64 cm long, 1 cm wide, and 180 μm thick piezoelectric film having the PQ direction making an angle of 45° with the RS direction was prepared in the same manner as in Example 1, except for using poly-D-lactic acid having an viscosity-average molecular weight of 320,000. The piezoelectric constants, dielectric constant, and elastic constant of the film were measured to obtain substantially the same results as in Example 1, except that the sign of the piezoelectric $d_{14}$ and $e_{14}$ constants was the reverse of that of poly-L-lactic acid.

EXAMPLE 3

Figure 8:
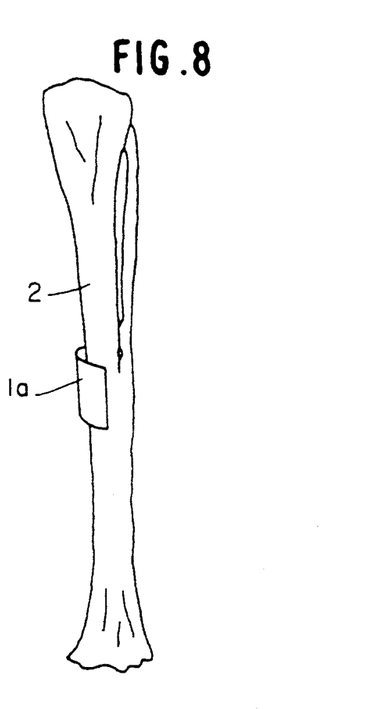
FIGS. 8 and 9 are perspective and sectional views, respectively, illustrating a use of a film of the polymeric piezoelectric material according to the present invention.
Figure 9:
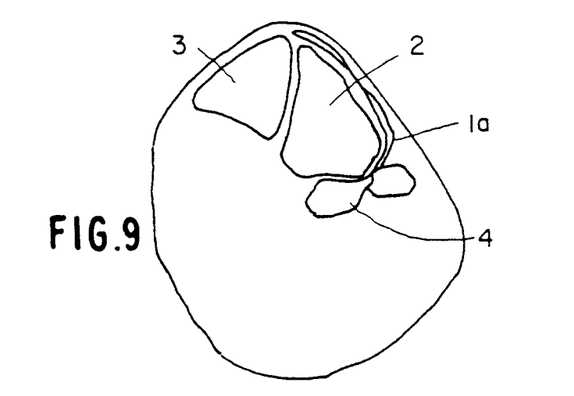

Osteotomoclosia was performed on the high tibia of a rabbit. As shown in FIGS. 8 (a side view of tibia) and 9 (a sectional view of tibia), film 1a obtained in Example 1 (cut at 45°) was loosely applied to the fractured part of tibia 2, and the film ends were fixed to the fascia of the tibialis anterior muscle 3 and the fascia of the flexor pollius longus 4 by sewing with a nylon yarn.

X-ray pictures of the fractured bone taken after 4 to 8 weeks from the operation demonstrated active callus formation and disappearance of the cut line of the bone. For comparison, the same osteotomoclosia was performed, but no film was applied. In this case, X-ray pictures revealed the cut line. It was thus proved that the piezoelectric film of uniaxially drawn polylactic acid accelerates initial osteosis ossification (formation of callus) in osteosynthesis on account of its piezoelectricity effect.

EXAMPLE 4

A poly-L-lactic acid film having been drawn at a draw ratio of 4 was cut at an angle of 45°, 0°, or 90° with the drawing direction to obtain a piezoelectric film. Each film was fixed to a fractured bone in the same manner as in Example 3. After 6 weeks from the osteotomoclosia, the fractured bone was roentgenologically observed. The X-ray picture of the fractured bone to which the 45°-cut film, which exhibits the highest piezoelectric properties, had been fixed demonstrated osteosis ossification on the periosteum and formation of cartilaginous phymas. The X-ray picture of the fractured bone to which the 0°-cut film had been fixed demonstrated only cartilaginous phymas but no ossification. In the case of the 90°-cut film, formation of cartilaginous phymas was not observed, nor was ossification observed. These results are correlated to the degree of the shear deformation of the film in conformity to the movement of the muscle to which each end of the film was fixed.

EXAMPLE 5

Figure 10:
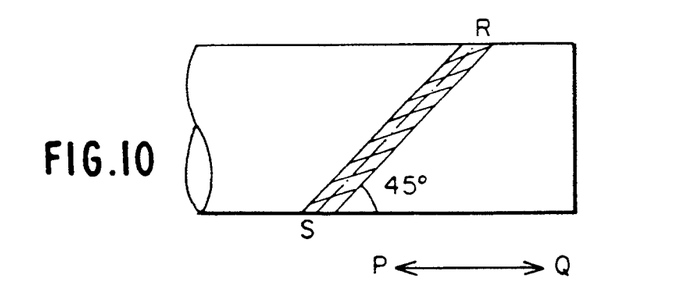
FIG. 10 is a side view illustrating a cutting mode of a rod of the polymeric piezoelectric material according to the present invention.
Figure 11:
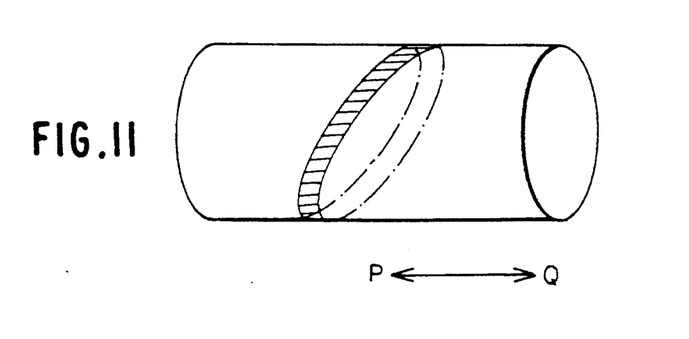
FIG. 11 is a perspective view illustrating a cutting mode of a rod of the polymeric piezoelectric material according to the present invention.

Poly-L-lactic acid having a viscosity-average molecular weight of 400,000 (in chloroform at 25° C.) was extruded to obtain a rod. The rod was drawn in the extrusion direction at a draw ratio of 5 in a heated nitrogen stream and sliced to a thickness of 1 mm at an angle of 45° with the drawing direction as shown in FIGS. 10 and 11. Both surfaces of the slice were polished to prepare a drawn film having a thickness of 60 μm.

The drawn film was cut into a square whose four sides were in a plane parallel to the drawing direction, and the cut film was adhered to a polymeric sound absorber. A plurality of electrodes were fixed to one of the two sides forming an angle of 45° with the drawing direction, and one electrode was fixed to the whole length of the other side. A water-resistant polymer membrane functioning as a matching layer was adhered to the drawn film on the face opposite to the sound absorber and on the sides thereof to prepare an ultrasonic transducer.

Ultrasonography was repeatedly performed on human bodies at the abdomen, the thyroid body, the breast, the uterus, etc. by means of an ultrasonic diagnostic machine using the above-prepared ultrasonic transducer. As a result, tomograms of very high resolving power were obtained.

EXAMPLE 6

A drawn film prepared in the same manner as in Example 5 was cut into a rectangle whose four sides were in a plane parallel to the drawing direction. An electrode was fixed to each of the facing sides forming an angle of 45° with the drawing direction, and the film was adhered to a rectangular support made of a polymer. The electrodes were connected to external connecting terminals to prepare an ultrasonic probe.

The ultrasonic probe was connected to a reflection type ultrasonic flaw detector and tested on sensitivity standard specimens for an ultrasonic flaw detection test at a frequency of 2 to 3 MHz. As a result, a satisfactory flaw pattern was obtained. Therefore, the ultrasonic probe was proved useful for flaw detection of steel materials, railroad tracks, water piping, walls of buildings, etc.

As described above, the polymeric piezoelectric materials according to the present invention are useful in various applications, such as implant devices for ossification acceleration, ultrasonic transducers for medical use, sound transducers, measuring instruments, ultrasonic wave applied measuring instruments, piezoelectric oscillators, mechanical filters, piezoelectric transformers, and the like.

While the invention has been described in detail and with reference to specific examples thereof, it will be apparent to one skilled in the art that various changes and modifications can be made therein without departing from the spirit and scope thereof.

What is claimed is:

1. A polymeric piezoelectric material comprising a polylactic acid molded article having been uniaxially drawn to an extent causing no fibrillation.

2. A polymeric piezoelectric material as claimed in claim 1, wherein said polylactic acid molded article has a piezoelectric constant $-d'_{14}$ of from 8 to 13 pC/N and a piezoelectric constant $-e'_{14}$ of from 10 to 20 mC/m².

3. A polymeric piezoelectric material as claimed in claim 1, wherein said polylactic acid molded article has (a) a thickness direction and (b) a drawing direction, and the drawing direction forms an angle other than 90° with the thickness direction.

4. A polymeric piezoelectric material as claimed in claim 1, wherein said polylactic acid molded article is a film.

5. A polymeric piezoelectric material as claimed in claim 4, wherein said film has (a) an axial direction which connects two ends of the film which are to be fixed and (b) a drawing direction, and the drawing direction forms an angle other than 90° with the axial direction.

6. A polymeric piezoelectric material as claimed in claim 1, wherein said polylactic acid molded article is a rod.

7. A polymeric piezoelectric material as claimed in claim 6, wherein said rod has (a) an axial direction which connects two ends of the rod and (b) a drawing direction, and the drawing direction forms an angle other than 90° with the axial direction.

8. A polymeric piezoelectric material as claimed in claim 1, wherein said polylactic acid molded article is a plate.

9. A polymeric piezoelectric material as claimed in claim 8, wherein said plate has (a) an axial direction which connects two ends of the plate and (b) a drawing direction, and the drawing direction forms an angle other than 90° with the axial direction.

10. A polymeric piezoelectric material as claimed in claim 1, wherein said polylactic acid molded article has a draw ratio of from 3 to 6.

11. A polymeric piezoelectric material as claimed in claim 10, wherein said polylactic acid molded article has a draw ratio of from 4 to 5.

12. A polymeric piezoelectric material as claimed in claim 1, wherein said polylactic acid molded article comprises a homopolymer of L- and D-lactic acid.

13. A polymeric piezoelectric material as claimed in claim 1, wherein said polylactic acid molded article comprises polylactic acid having a viscosity-average molecular weight of from 50,000 to 1,000,000.

14. A polymeric piezoelectric material as claimed in claim 1, wherein the polylactic acid molded article is formed by extrusion at a temperature between the melting point of polylactic acid and 220° C.

15. A polymeric piezoelectric material as claimed in claim 1, wherein the polylactic acid molded article is drawn at a temperature of from 60 to 180° C.

16. A polymeric piezoelectric material as claimed in claim 1, wherein the polylactic acid molded article is a film having a thickness ranging from 50 to 500 μm.

17. A method for treating a fractured bone, comprising (A) forming a polymeric piezoelectric material comprising a polylactic acid film having been uniaxially drawn to an extent causing no fibrillation,
wherein the film has a piezoelectric constant $-d'_{14}$ of from 8 to 13 pC/N and a piezoelectric constant $-e'_{14}$ of from 10 to 20 mC/m², and
wherein the film has (a) an axial direction which connects two ends of the film which are to be fixed and (b) a drawing direction, and the drawing direction forms an angle other than 90° with the axial direction, and
(B) applying the film to a bone having a fracture part, with said two ends of the film which are to be fixed being fixed near the fractured part for acceleration of ossification.

18. A method of using a polymeric piezoelectric material, comprising using said material as a piezoelectric element of an ultrasonic transducer of an ultrasonographic device,
   wherein the material comprises a polylactic acid molded article having been uniaxially drawn to an extent causing no fibrillation,
   wherein the polylactic acid molded article has a piezoelectric constant $-d'_{14}$ of from 8 to 13 pC/N and a piezoelectric constant $-e'_{14}$ of from 10 to 20 mC/m$^2$, and
   wherein the polylactic acid molded article has (a) a thickness direction and (b) a drawing direction, and the drawing direction forms an angle other than 90° with the thickness direction.

19. A method of using a polymeric piezoelectric material, comprising using said material as a piezoelectric element of an ultrasonic probe of an ultrasonic flaw detector,
   wherein the material comprises a polylactic acid molded article having been uniaxially drawn to an extent causing no fibrillation,
   wherein the polylactic acid molded article has a piezoelectric constant $-d'_{14}$ of from 8 to 13 pC/N and a piezoelectric constant $-e'_{14}$ of from 10 to 20 mC/m$^2$, and
   wherein the polylactic acid molded article has (a) a thickness direction and (b) a drawing direction, and the drawing direction forms an angle other than 90° with the thickness direction.

* * * * *